United States Patent [19]

Tóth et al.

[11] Patent Number: 5,350,872
[45] Date of Patent: Sep. 27, 1994

[54] PROCESS FOR THE PREPARATION OF CARBOXYLIC ACIDS AND DERIVATIVES OF THEM

[75] Inventors: György Tóth, Nyiregyháza; János Bálint, Debrecen; Klára Elek Née Herczik, Debrecen; Zsuzsanna Móricz née Garai, Debrecen; Éva Mudra née Kántor, Ebes, all of Hungary

[73] Assignee: Biogal Gyogyszergrar, Debrecen, Hungary

[21] Appl. No.: 143,124

[22] Filed: Oct. 29, 1993

Related U.S. Application Data

[62] Division of Ser. No. 928,247, Aug. 11, 1992.

[51] Int. Cl.$^5$ ............................................. C07C 69/76
[52] U.S. Cl. .................................... 560/55; 560/9; 560/17; 560/20; 560/54; 560/76; 560/103; 560/105; 560/190; 562/434; 562/459; 562/465; 562/480; 562/495; 562/568; 562/571; 562/590; 562/606
[58] Field of Search ............... 560/55, 9, 17, 20, 54, 560/76, 103, 105, 190; 562/434, 459, 465, 480, 495, 568, 571, 590, 600

[56] References Cited

PUBLICATIONS

J.A.C.S. 80(4) p. 933 1958.
Textrahedron Lett. 80(1) p. 759 1978.
Tetrahedron Lett 24(1983) 4 p. 951.

*Primary Examiner*—Paul J. Killos
*Attorney, Agent, or Firm*—Keil & Weinkauf

[57] ABSTRACT

The subject matter of the invention is a process for the preparation of carboxylic acids and derivatives of them of the general formula

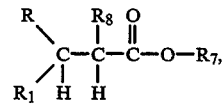

wherein
R means hydrogen, or a $C_{1-4}$alkyl or a ($C_{1-5}$alkoxy)-carbonyl group,
$R_1$ is as defined in claim 1,
$R_7$ stands for hydrogen or a $C_{1-7}$alkyl group and
$R_8$ means hydrogen or a carboxyl group, by reacting a 1,3-dioxane-4,6-dione derivative of the general formula

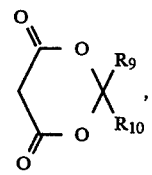

wherein
$R_9$ stands for a $C_{1-4}$alkyl group or a phenyl group, optionally monosubstituted by halogen and
$R_{10}$ stands for hydrogen or a $C_{1-5}$alkyl group or
$R_9$ and $R_{10}$ together form a pentamethylene group, and an aldehyde or ketone of the general formula

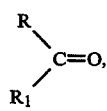

in the presence of formic acid.

9 Claims, No Drawings

PROCESS FOR THE PREPARATION OF CARBOXYLIC ACIDS AND DERIVATIVES OF THEM

This is a divisional application of Ser. No. 07/928,247, filed Aug. 11, 1992.

This invention relates to a novel process for the preparation of carboxylic acids and derivatives of them playing an important role in the production of fine chemicals and drugs and in organic syntheses. More particularly, the invention is concerned with a new process for the preparation of carboxylic acids and derivatives of them of the general formula

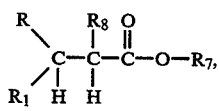

wherein

R means hydrogen, or a $C_{1-4}$alkyl or a $(C_{1-5}$ alkoxy)-carbonyl group, $R_1$ stands for a $C_{1-6}$alkyl group, a $(C_{1-5}$alkoxy)-carbonyl group, a $(C_{1-5}$alkyl)carbonyl group, a $(C_{1-5}$alkoxy)carbonyl$(C_{1-4}$alkyl) group, a phenyl group, optionally monosubstituted by a $C_{1-4}$ alkyl or $C_{2-4}$alkenyl group, di- or tri-substituted by $C_{1-4}$alkoxy groups, monosubstituted by a nitro group, disubstituted by $C_{1-4}$alkoxy and hydroxy groups, monosubstituted by a $C_{1-4}$alkylthio group, mono- or disubstituted by [a] di($C_{1-4}$alkyl)amino group(s) or monosubstituted by halogen, for a furyl group, for a thiofuryl group, for a thienyl group, or for a group of the formula

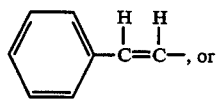

R and $R_1$ together form a straight-chain $C_{4-5}$alkylene group, $R_7$ stands for hydrogen or a $C_{1-7}$alkyl group and $R_8$ means hydrogen or a carboxyl group.

According to he Prior Art, compounds of the general formula I, wherein $R_7$ means an alkyl group and $R_8$ means a carboxyl group, are prepared by reacting an aldehyde or ketone of the general formula

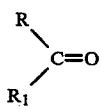

wherein

R and $R_1$ are as above defined, with a dialkyl malonate in a Knoevenagel-Doebner type reaction, then reducing the obtained dialkyl alkylidenemalonate, e.g. with sodium borohydride, (J. Org. Chem. 31 [1966], 620) to give the respective monosubstituted dialkyl malonate and hydrolyzing the latter with 1 molar equivalent of alkali metal hydroxide to obtain the monosubstituted monoalkyl malonate [(I), $R_7$=alkyl group and $R_8$=carboxyl group].

This compound can be prepared also by using a Meldrum's acid derivative of the general formula

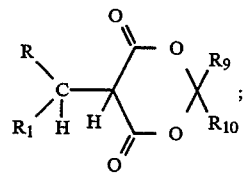

wherein

R and $R_1$ are as defined above for formula I, $R_9$ stands for a $C_{1-4}$alkyl group or a phenyl group, optionally monosubstituted by halogen and $R_{10}$ stands for hydrogen or a $C_{1-5}$alkyl group or $R_9$ and $R_{10}$ together form a pentamethylene group, as starting substance, which is treated with the alcoholic solution of 1 molar equivalent of sodium alkoxide (J. Amer. Chem. Soc. 80, [1958], 4 933).

Compounds of the general formula I, wherein $R_7$ means an alkyl group and $R_8$ is hydrogen, can be prepared by the thermal decarboxylation of compounds of the general formula I, wherein $R_7$ means an alkyl group and $R_8$ is a carboxyl group, or by boiling the Meldrum's acid derivative of general formula V in a 10:1 mixture of pyridine and ethanol in the presence of copper powder (Tetrahedron Lett. [1978], 1 759).

Compounds of the general formula I wherein both $R_7$ and $R_8$ are hydrogen, are most simply prepared by hydrolyzing the respective $\alpha,\beta$-saturated carboxylic acid ester [(I) $R_7$=alkyl group and $R_8$=H].

According to another known process for preparing these compounds an aldehyde of the general formula II is reacted with malonic acid in a Knoevenagel-Doebner reaction, i.e. in pyridine, in the presence of piperidinium acetate as catalyst at room temperature for 3 weeks or at 100° C. for 1 to 18 hours (Org. Reactions 1, [1942], 210), then the double bond of the $\alpha,\beta$-unsaturated carboxylic acid formed in the above reaction is saturated.

Also the Meldrum's acid derivative of the general formula V can be transformed to the carboxylic acid of general formula I in which $R_7=R_8=H$ by boiling it with a mixture of acetic acid and 10% aqueous hydrogen bromide solution for 2 hours (Monatsh. Chem. 95, [1964], 1 283).

Meldrum's acid derivatives of the general formula V used as starting substances in the above reactions can be prepared in several ways.

According to one of these methods a 1,3-dioxane-4,6-dione derivative of the general formula

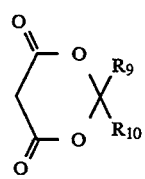

wherein $R_9$ and $R_{10}$ are as above defined,
is reacted with an aldehyde or ketone of the general formula II (Chemia 24, [1970], 65), then the double bond of the unsaturated compound of general formula

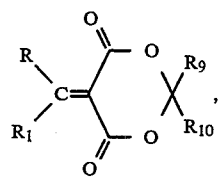

thus formed is saturated with hydrogen to give the respective Meldrum's acid derivative of general formula V.

The Meldrum's acid derivative of general formula V can directly be synthetized from aldehydes or ketones of the general formula II and oxo compounds of the general formula III by reacting the components in the presence of piperidinium acetate and sodium hydrogen telluride (Synth. Commun. 16, [1986], 1 701) or without piperidinium acetate in the presence of borohydride-dimethylamine (Tetrahedron Lett. 24, [1983], 4 951).

Thus, it can be stated that numerous processes are known for the preparation of compounds of the general formula I. However, when a compound of the general formula II and malonic acid or a malonic acid derivative are used as starting substances, the synthesis involves at least two steps and, in addition, it contains in each case a reduction step being dangerous concerning the working phases, reagents and catalysts. Another difficulty is that the selectivity of the reduction step for the ,β-position should be assured since the molecule to be reduced contains more than one double bond (the C=O bond of the carboxyl group should not be reduced) and optionally, the molecule may be substituted by a readily reducible functional group, e.g. a nitro group.

The Meldrum's acid derivatives of general formula V used as starting substances can be prepared by the reduction of compounds of the general formula IV. This reduction is also difficult to carry out since both compounds of general formulae IV and V are heat-sensitive and liable to decomposition. The 1,3-dioxane-4,6-dione derivatives are usually unstable to heat; thus, the reaction rate cannot unrestrictedly be increased by elevating the temperature, the yields are mostly low and, due to the decomposition, the product obtained contains contaminations. At the same time the difficulty arises also here that the reduction should selectively be carried out in such a way that the C=C double bond is reduced but neither the C=O double bond nor a nitro group being optionally present are affected.

In both cases the reduction requires an appropriate investment and safety measures. The accomplishment at a higher scale of these reductions is problematic. For the catalytic hydrogenation a complicated and expensive equipment is required and the metal catalysts (e.g. palladized charcoal) are in general inflammable. Other specific reducing agents such as hydrides commonly involve the risk of fire and explosion; the reduction should be carried out under an inert gas, the reagents require extreme caution from labour-safety point of view and are difficult to handle.

The problem underlying to the invention is to create a process for selectively preparing the carboxylic acids and derivatives of them of general formula I from oxo compounds of the general formula II assuring the selectivity of the reduction to the ,β-position by using cheap and safe reagents in a simple equipment by a "one-pot" method, without separating the intermediates, thus eliminating the drawback of the reduction methods discussed above, in which process further it is provided for the possibility to decide in advance the formation of one defined group of compounds of the three substance classes within the compounds of general formula I, namely the preparation of a carboxylic acid [I with $R_7=R_8=H$] or carboxylic acid ester [I with $R_7$=alkyl group, $R_8$=H] or monoalkyl malonate [I with $R_7$=alkyl group,

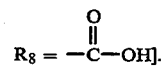

The above surprisingly has been achieved by the invention.

The invention is based on the recognition that the ring of 1,3-dioxane-4,6-dione compounds (Meldrum's acid derivatives) of the general formula V can easily and simply be opened and the dicarboxylic acid formed can easily and simply be decarboxylated in the presence of a mixture of formic acid and a secondary or tertiary amine; in addition, the free carboxyl group can also very simply be esterified simultaneously with the opening of the ring of 1,3-dioxane-4,6-diones.

Formic acid is a known reducing agent in the chemical literature, but in itself it is not capable to cleave the 1,3-dioxane-1,4-dione ring of the Meldrum's acid derivatives of general formula V and to decarboxylate the carboxylic acid obtained. Thus, it could not be expected that it could implement each of the above transformations in the presence of a secondary or tertiary amine.

Thus, the subject matter of the present invention is a new process for the preparation of carboxylic acids and derivatives of them of the general formula

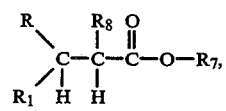

wherein

R means hydrogen, or a $C_{1-4}$alkyl or a $(C_{1-5}$alkoxy)-carbonyl group, $R_1$ stands for a $C_{1-6}$alkyl group a $(C_{1-5}$alkoxy)-carbonyl group, a $(C_{1-5}$alkyl)carbonyl group, a $(C_{1-5}$alkoxy)carbonyl$(C_{1-4}$alkyl) group, a cyclohexyl group, a cyclopentyl group, a phenyl group, optionally monosubstituted by a $C_{1-4}$alkyl or $C_{2-4}$alkenyl group, di- or tri-substituted by a $C_{1-4}$alkoxy groups, monosubstituted by a nitro group, disubstituted by $C_{1-4}$alkoxy and hydroxy groups, monosubstituted by a $C_{1-4}$alkylthio group, mono- or disubstituted by fay di($C_{1-4}$alkyl)amino group(s) or monosubstituted by halogen, for a furyl group, for a thiofuryl group, for a thienyl group, or for a group of the formula

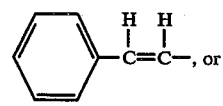

R and $R_1$ together form a straight-chain $C_{4-5}$alkylene group, $R_7$ stands for hydrogen or a $C_{1-7}$alkyl group and $R_8$ means hydrogen or a carboxyl group, which is characterized by reacting a 1,3-dioxane-4,6-dione derivative (Meldrum's acid derivative) of the general formula

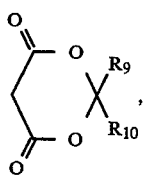   III wherein
$R_9$ stands for a $C_{1-4}$alkyl group or a phenyl group, optionally monosubstituted by halogen and
$R_{10}$ stands for hydrogen or a $C_{1-5}$alkyl group or
$R_9$ and $R_{10}$ together form a pentamethylene group,
and an aldehyde or ketone of the general formula

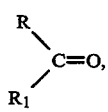   II wherein
R and $R_1$ are as defined above,
in the presence of formic acid and of 1 or more secondary and/or tertiary amine(s) and, if desired, of an alcohol of the general formula $R_7$—OH   VI, wherein
$R_7$ is a $C_{1-7}$alkyl group,
at a temperature of 20° to 140° C., optionally in the presence of 1 or more inert organic solvent(s),
and/or
reducing an unsaturated 1,3-dioxane-4,6-dione derivative of the general formula

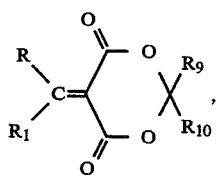   IV wherein
R, $R_1$, $R_9$ and $R_{10}$ are as defined above,
and/or
a 1,3-dioxane-4,6-dione derivative of the general formula

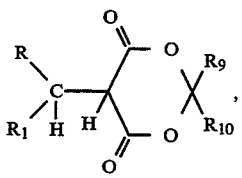   V wherein
R, $R_1$, $R_9$ and $R_{10}$ are as defined above, with formic acid in the presence of 1 or more secondary and/or tertiary amine(s) and, if desired, of an alcohol of the general formula $R_7$—OH   VI, wherein
$R_7$ is a $C_{1-7}$alkyl group,
at a temperature of 20° to 140° C., optionally in the presence of 1 or more inert organic solvent(s).

Thus, the preparation of one defined type of the compounds of general formula I can be decided by selection of the reaction medium and temperature used.

When the reaction carried out in an alcoholic medium is terminated by evaporating the alcohol under reduced pressure at a temperature of at most 70° C., a monoalkyl malonate derivative dicarboxylic acid alkyl ester derivative: [I with $R_7$=alkyl group, $R_8$=carboxyl group is obtained. When, after evaporating the alcohol, the temperature of the reaction mixture is increased to at most 140° C., suitably to 110° to 130° C., a carboxylic acid alkyl ester [I with $R_7$=alkyl group, $R_8$=H] is obtained.

On carrying out the reaction in the absence of alcohol at a temperature of 60° to 140° C., suitably at 90° to 100° C., a dicarboxylic acid [I with $R_7$=H, $R_8$=carboxyl group] is formed as intermediate, which is immediately decarboxylated to the monocarboxylic acid [I with $R_7$=$R_8$=H].

In case of carrying out the reaction in an alcoholic medium in the presence or a lower alkoxide, for example, sodium ethoxide, and then adding an aqueous alkali hydroxide solution for example, sodium hydroxide solution applying mild conditions a dicarboxylic acid [I with $R_7$=H, $R_8$=carboxyl group] can be isolated.

In this description alkyl group means a straight or branched chain alkyl group, such as methyl, ethyl, propyl, isopropyl, butyl, isobutyl, tert-butyl or sec-butyl group.

The process according to the invention is preferably used for the preparation of carboxylic acids and derivatives of them of the general formula I,
wherein
R means a $C_{1-4}$alkyl or a ($C_{1-4}$alkoxy)carbonyl group;
$R_1$ stands for a $C_{1-5}$alkyl group, a ($C_{1-4}$alkoxy)carbonyl group, a ($C_{1-4}$alkyl)carbonyl group, a ($C_{1-4}$alkoxy)carbonyl($C_{1-4}$alkyl) group, a phenyl group, optionally monosubstituted by a $C_{1-4}$alkyl group, di- or trisubstituted by $C_{1-4}$alkoxy groups, monosubstituted by a nitro group, disubstituted by $C_{1-4}$alkoxy and hydroxy groups, monosubstituted by a $C_{1-4}$alkylthio group, mono- or disubstituted by [a] di($C_{1-4}$alkyl)amino group(s) or monosubstituted by halogen, for a furyl group, for a thienyl group, or for a group of the formula

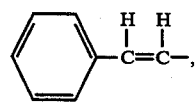

$R_7$ stands for hydrogen or a $C_{1-4}$alkyl group and
$R_8$ means hydrogen or a carboxyl group.
Preferably the $C_{1-4}$alkyl group which may be represented by R is such having from 1 to 3, particularly 1 or 2, carbon atom(s).

Furthermore it is preferred that the ($C_{1-5}$alkoxy) carbonyl group which may be represented by R is such with an alkoxy part having from 1 to 4, particularly 1 to 3, most particularly 1 or 2, carbon atom(s).

Preferably the $C_{1-6}$alkyl group which may be represented by $R_1$ is such having from 1 to 5, particularly 1 to 4, most particularly 1 to 3, above all 1 or 2, carbon atom(s).

Moreover it is preferred that the alkyl and/or alkoxy part(s) occurring in groups which may be represented by $R_1$ is/are such having from 1 to 3, particularly 1 or 2, carbon atom(s).

It is also preferred that the $C_{2-4}$alkenyl group by which the phenyl group which may be represented by $R_1$ may be substituted is such having from 2 or 3, particularly 2, carbon atoms.

Preferably the halogen by which the phenyl group which may be represented by $R_1$ may be substituted is fluorine or chlorine.

Furthermore it is preferred that the $C_{1-4}$alkyl group which may be represented by $R_7$ is having from 1 to 3, particularly 1 or 2, carbon atom(s).

Preferably the $C_{1-4}$alkyl group which may be represented by $R_9$ is such having from 1 to 3, particularly 1 or 2, carbon atom(s).

Moreover it is preferred that the halogen by which the phenyl group which may be represented by $R_9$ may be substituted is fluorine or chlorine.

Preferably the $C_{1-5}$alkyl group which may be represented by $R10$ is such having from 1 to 5, particularly 1 to 4, most particularly 1 to 3, above all 1 or 2, carbon atom(s).

The preparation of the carboxylic acids and derivatives of them of general formula I can be started from a mixture containing the compounds of general formulae II and III or from the compounds of formula IV or V. The mixture of formic acid and the secondary and/or tertiary amine(s) simultaneously catalyzes the formation of compound of the general formula IV from the compounds of formulae II and III, as well as the selective reduction of the compound of general formula IV to the compound of general formula V and the cleavage of the dioxane ring of the compound of general formula V.

The success of the consecutive reaction is mainly determined by the first reaction step, i.e. by the readiness of formation of the intermediate of general formula IV. The reaction of aldehydes with the 1,3-dioxane-4,6-dione derivatives of general formula III is rapid, whereas that of ketones is slower.

The reduction step of the reaction route, i.e. the formation of the 1,3-dioxane-4,6-dione compound of general formula V from the corresponding unsaturated compound of general formula IV, is selective since only the double bond in position 5 of the 1,3-dioxane-4,6-dione ring is saturated by hydrogen. The nitro group, which is otherwise easy to reduce, is not reduced. In this reaction no hydrogen evolves, wherefore the process can be safely carried out. No particular safety systems, which are required e.g. for the catalytic hydrogenation, should be arranged.

Formic acid alone is not suitable to catalyze the above reactions. For this purpose the presence of a secondary and/or tertiary amine is also necessary.

Suitably also a mixture of formic acid and [a] secondary and/or tertiary amine(s) recovered after the reaction, for example by distillation, can be used.

Suitably [a] di- and/or tri-($C_{1-4}$alkyl)amine(s) and/or cyclic amine(s) is/are used as secondary and/or tertiary amine(s).

Preferably dimethylamine, diethylamine, methylethylamine, triethylamine, pyridine, piperidine, [an] N-($C_{1-4}$alkyl)piperidine(s) and/or morpholine is/are used as /a/ secondary and/or tertiary amine(s). Particularly preferably piperidine is used as a tertiary amine.

A further particularly preferred tertiary amine is triethylamine.

Preferably benzene, dimethylformamide, acetonitrile and/or ethyl acetate is/are used as [an] inert organic solvent(s).

It is necessary to use at least 1 mole of formic acid related to 1 mole of compound of general formula III or IV or V, but an excess of formic acid is desirable. Formic acid is preferably used in an amount of 1 to 20, more preferably 6 to 12, most preferably 5 to 6 mole(s), calculated for the compound of general formula III, IV or V.

The molar ratio of the secondary and/or tertiary amine(s) to the formic acid can be varied between wide limits. It is suitable to use 0.1 to 1 mole, preferably 0.1 to 0.5 mole, of [a] secondary and/or tertiary amine(s) calculated for 1 mole of formic acid. When using triethylamine, the molecular compound of formula $[(C_2H_5)_3N]_2 \cdot [HCOOH]_5$ corresponding to the molar ratio of 1:0.4 has an outstanding role.

In case of starting from compounds of formulae II and III preferably they are used in equimolar quantities.

When the aim is to prepare an unesterified carboxylic acid, the reaction can be accomplished without any solvent in a mixture containing the secondary and/or tertiary amine(s), preferably triethylamine and formic acid, but [an] inert organic solvent(s), e.g. benzene, dimethylformamide, acetonitrile and/or ethyl acetate, can also be employed for the reaction. When the aim is to form a carboxylic acid of formula I with $R_7=R_8=H$, the process can be made more economical by utilizing in a next reaction the mixture of formic acid and triethylamine after carrying out the reaction.

When reacting Meldrum's acid (formula III with $R_9=R_{10}=$methyl group) and veratraldehyde as model compounds in the mixture of formic acid and triethylamine at a temperature of 75° to 120° C. for 1 to 4 hours, 3,4-di-(methoxy)-hydrocinnamic acid {3-[3',4'-di-(methoxy)-phenyl]-propionic acid}is obtained. The analysis of this reaction showed that in the first step 5-[3',4'-di-(methoxy)-phenylmethylene]-Meldrum's acid is formed in a rapid reaction, which is transformed to 5-[3',4'-di-(methoxy)-phenylmethyl]-Meldrum's acid by saturation of the double bond in the second step. The formation of the final product can be interpreted in such a way that the dioxane ring of 5-[3',4'-di-(methoxy)-phenylmethyl]-Meldrum's acid is opened while acetone and 3,4-di-(methoxy)-benzylmalonic acid are formed. The decarboxylation of the latter compound results in 3,4-dimethoxyhydrocinnamic acid. The above-discussed route of the overall reaction has been proven by separation and identification of the intermediates and also by the experimental facts that 3,4-di-(methoxy)-cinnamic acid could not be hydrogenated to 3,4-di-(methoxy-hydrocinnamic acid when using formic acid and triethylamine reagents.

By boiling Meldrum's acid (formula III with $R_9=R_{10}=$methyl group) with veratraldehyde in an ethanolic medium in the presence of formic acid and triethylamine, monoethyl 3,4-di-(methoxy)-benzylmalonate was obtained. According to our experimental observation, diethyl 3,4-di-(methoxy)-benzylidene malonate could not be hydrogenated to diethyl 3,4-di-(methoxy)-benzylmalonate when using formic acid and triethylamine as reagents. Further on we have observed that by reacting veratraldehyde with Meldrum's acid, formic acid and triethylamine at 100° C. for 2 hours and then by boiling with ethanol for 2 hours 3,4-dimethoxyhydrocinnamic acid and not ethyl 3,4-di-(methoxy)-hydrocinnamate was obtained as final product. Thus, the reaction can be interpreted only in such a way that 5-[3',4'-di-(methoxy)-phenylmethyl]-Meldrum's acid is formed in the manner described above, the dioxane ring of which is opened and one carboxyl group of the 3,4-di-(methoxy)-benzylmalonic acid formed is simultaneously esterified. When the temperature of the reaction mixture is increased after removing the ethanol, the carboxyl group is eliminated and 3,4-di-(methoxy)-hydrocinnamic acid ester is obtained.

The carboxylic acids and derivatives of them of general formula V can preferably be prepared by reducing a compound of the general formula IV, wherein R, $R_1$, $R_9$ and $R_{10}$ are defined above, in the presence of formic acid and a secondary or tertiary amine.

The compounds of general formula IV can suitably be prepared by reacting an oxo compound of the general formula II, wherein R and $R_1$ are as defined above, with a 1,3-dioxane-4,6-dione derivative of the general formula III, wherein $R_9$ and $R_{10}$ are as defined above, in the presence of a mixture of formic acid and a secondary or tertiary amine.

The preparation of the 1,3-dioxane-4,6-dione derivatives of general formula III was described by H. McNab in Chem. Soc. Rev. 7, [1978], 345 to 358.

The aldehydes and ketones of general formula II are commercially available.

The process of the invention is illustrated in more detail by the following Examples.

EXAMPLE 1

Preparation of 3-(3,4-dimethoxyphenyl)propionic acid 24.3 g (33.6 ml, 0.24 mol) of triethylamine were dropwise added to 27.6 g (22.6 ml, 0.6 mol) of formic acid while stirring and cooling to give a mixture of 50 ml volume.

To a flask equipped with a stirrer and condenser, 7.2 g (0.05 mol) of 2,2-dimethyl-1,3-dioxane-4,6-dione (Meldrum's acid), 8.3 g (0.05 mol) of veratraldehyde and 50 ml of the mixture of formic acid and triethylamine prepared as described above were weighed in. After heating the reaction mixture to 100° C. during 1 hour and then maintaining at the same temperature for 2 hours, the reaction mixture was cooled to room temperature, 75 ml of water were added, the pH value was adjusted to 1 with concentrated hydrochloric acid and the mixture was extracted twice with 50 ml of chloroform each. After combining, the chloroform extract was washed twice with 100 ml of 1 N sodium hydroxide solution each, then the combined aqueous alkaline phase was shaken twice with 50 ml of chloroform each. The aqueous phase was stirred with 0.5 g of activated charcoal at room temperature for 30 minutes. After filtering off the charcoal, 20 g of ice were added to the filtrate and the pH value was adjusted to 1 by adding concentrated hydrochloric acid. After standing at 5° C. for 16 hours the precipitate was filtered, washed 3 times with water on the filter and dried at 40° C. under reduced pressure.

A yield of 8.2 g (78%) was achieved, m.p.: 97°–97.5° C.

After combining the aqueous mother liquor and the washing liquor of the main product, extraction was carried out by using 2×50 ml of chloroform. The combined chloroform extract was dried over anhydrous sodium sulfate and filtered. After evaporating the filtrate under reduced pressure until chloroform-free, the evaporation residue was crystallized from aqueous methanol of 50% by volume.

Thus, a yield of 0.75 g (7.1%) was obtained, m.p.:96°–97° C.

The literature m.p. is 96°–97° C. (see: Handbook of Data on Organic Compounds).

The infrared spectrum of the first crop (8.2 g) was found to be completely identical to that of the second crop (0.75 g). The overall yield amounted to 8.95 g (85.1%).

The product obtained had the following quality characteristics:

IR (KBr): 1700 cm$^{-1}$ (CO)

$^1$H-NMR (CDCl$_3$, δ ppm): 2.66 (t, 2H, CH$_2$), 2.93 (t, 2H, CH$_2$), 3.86 (s, 6H, 2OCH$_3$), 6.80 (m, 3H, aromatic).

EXAMPLE 2

Preparation of 3-(3,4-dimethoxyphenyl)propionic acid

After weighing 14.4 g (0.1 mol) of Meldrum's acid and 16.6 g (0.1 mol) of veratraldehyde to 50 ml of the mixture of formic acid and triethylamine prepared according to Example 1, the reaction mixture was heated to 90° C. during 1 hour and maintained at 90° C. for 2 hours. After cooling down to room temperature 200 ml of ice-water were added to the reaction mixture, the pH value was adjusted to 1 by adding concentrated hydrochloric acid and the mixture was let stand at 5° C. for 16 hours. After filtration the precipitate was washed 3 times on the filter and dried at 40° C. under reduced pressure.

A yield of 15.7 g (74.7%) was obtained, m.p.: 94°–96° C.

After recrystallizing a small sample of the product from aqueous methanol of 50% by volume, the melting point rose to 96°–97.5° C.

The aqueous mother liquor and washings of the first crop were combined and extracted twice with 50 ml of chloroform each. After combining, the chloroform phase was extracted twice with 50 ml of 1 N sodium hydroxide solution each. The combined alkaline aqueous phase was extracted twice with 50 ml of chloroform each. After stirring with 0.2 g of activated charcoal at room temperature for 30 minutes, the aqueous phase was filtered, the pH value of the filtrate was acidified to 1 with hydrochloric acid and the mixture was allowed to stand at 5° C. for 16 hours. After filtration the precipitate was washed 3 times with water and dried.

A yield of 2.1 g (10%) was obtained, m.p.: 96°–97° C.

The quality characteristics of the products obtained were identical to those given in Example 1. An overall yield of 17.8 g (84.7%) was achieved.

EXAMPLE 3

Preparation of 3-(3,4-dimethoxyphenyl) propionic acid

After weighing 7.2 g (0.05 mol) of Meldrum's acid and 8.3 g (0.05 mol) of veratraldehyde to 50 ml of the mixture of formic acid and triethylamine prepared according to Example 1, the reaction mixture was heated to 100° C. during 1 hour and maintained at the same temperature for further 1 hour. Then the excess of formic acid and triethylamine was distilled off under reduced pressure of 2 kPa to give a distillate of 40 ml volume. The distillation residue was dissolved in 100 ml of chloroform and extracted with 50 ml of 1 N sodium hydroxide solution. The chloroform phase was extracted with 2×100 ml of 1 N sodium hydroxide solution. Thereafter Example 1 was followed to give a yield of 8.6 g (81.8%), m.p.: 96°–97° C.

EXAMPLE 4

Preparation of 3-(3,4-dimethoxyphenyl)propionic acid 7.2 g (0.05 mol) of Meldrum's acid and 8.3 g (0.05 mol) of veratraldehyde were weighed to 40 ml of the mixture of formic acid and triethylamine recovered by distillation in Example 3. The reaction was carried out and the final product was separated as described in Example 3. The volume of the mixture of formic acid and triethylamine recovered amounted to 28 ml.

A yield of 8.4 g (79.9%) was achieved, m.p.: 96°–97.5° C.

EXAMPLE 5

Preparation of 3-(3,4-dimethoxyphenyl) propionic aced

After dropwise adding 19 g (19.3 ml, 0.24 mol) of pyridine to 27.6 g (22.6 ml, 0.6 mol) of formic acid under stirring and cooling, 14.6 g (0.05 mol) of 5-(3,4-dimethoxyphenylmethylene)-2,2-dimethyl-1,3-dioxane-4,6-dione (m.p.: 173° C.) were weighed to the solution obtained. Thereafter Example 1 was followed by using a reaction time of 2.5 hours.

The title compound was obtained, m.p.: 95°–97° C.

EXAMPLE 6

Preparation of 3-(3,4-dimethoxyphenyl)propionic acid

After weighing 14.6 g (0.05 mol) of 5-(3,4-dimethoxyphenylmethylene)-2,2-dimethyl-1,3-dioxane-4,6-dione (m.p.: 173° C.) to 50 ml of the mixture of formic acid and triethylamine prepared according to Example 1, the procedure described in Example 1 was followed.

An overall yield of 9.4 g (89.4%) was achieved, m.p.: 97°–97.5° C.

EXAMPLE 7

Preparation of 3-(3,4-dimethoxyphenyl)propionic acid

After adding 2.5 ml of the mixture of formic acid and triethylamine prepared according to Example 1 to 2.94 g (0.01 mol) of 5-(3,4-dimethoxyphenylmethyl)-2,2-dimethyl-1,3-dioxane-4,6-dione (m.p.: 142°–144° C.), the reaction mixture was heated to 100° C. for 2 hours, then cooled down. After the addition of 25 ml of water the pH value was adjusted to 1 by adding concentrated hydrochloric acid, then the mixture was thoroughly shaken with 100 ml of chloroform. After separation the chloroform phase was evaporated under reduced pressure to give a white crystalline product.

A yield of 1.94 g (92.3%) was obtained, m.p.: 95°–97° C.

EXAMPLE 8

Preparation of 3-(3,4-dimethoxyphenyl)propionic acid 25 ml of the mixture of formic acid and triethylamine prepared as described in Example 1 were added to a mixture of 4.8 g (0.025 mol) of 2-phenyl-1,3-dioxane-4,6-dione (m.p.: 148° C.) and 4.15 g (0.025 mol) of veratraldehyde. The reaction was carried out according to Example 1.

A yield of 3.1 g (59.0%) was achieved, m.p.: 95.5°–97.5° C.

EXAMPLE 9

Preparation of 3-(3,4-dimethoxyphenyl)propionic acid 5.26 g (0.025 mol) of 2-(4-fluorophenyl)-1,3-dioxane-4,6-dione (m.p.: 166°–167° C.) and 4.15 g (0.025 mol) of veratraldehyde were added to 25 ml of the mixture of formic acid and triethylamine prepared as described in Example 1. The reaction was carried out according to Example 1.

A yield of 3.05 g (58%) was obtained, m.p.: 94°–96° C.

EXAMPLE 10

Preparation of 3-(3,4-dimethoxyphenyl)propionic acid 4.60 g (0.025 mol) of 2,2-pentamethylene-1,3-dioxane-4,6-dione (m.p.: 94° C.) and 4.15 g (0.025 mol) of veratraldehyde were added to 25 ml of the mixture of formic acid and triethylamine prepared as described in Example 1. The reaction was carried out according to Example 1.

A yield of 3.2 g (60.9%) was achieved, m.p.: 95°–97° C.

EXAMPLE 11

Preparation of 3-(3,4-dimethoxyphenyl)propionic acid 25 ml of the mixture of formic acid and triethylamine prepared as described in Example 1 were added to 8.31 g (0.025 mol) of 5-(3,4-dimethoxyphenylmethylene)-2,2-pentamethylene-1,3-dioxane-4,6-dione (m.p.: 148°–150° C.). The reaction was carried out according to Example 1.

A yield of 3.75 g (71.3%) was achieved, m.p.: 96°–97.5° C.

EXAMPLE 12

According to the method of Example 1 50 ml of the mixture of formic acid and triethylamine and 7.2 g (0.05 mol) of Meldrum's acid were weighed in, but 0.05 mol of an other aldehyde was used instead of veratraldehyde to give the results summarized in the next Table.

| | | $R_1$—CH$_2$—CH$_2$—COOH [I, R=R$_7$=R$_8$=H] | | |
|---|---|---|---|---|
| Example No. | $R_1$ | Yield, % | M.p. °C. | Literature m.p. °C. |
| 12a | 3,4,5-trimethoxyphenyl | 82.4 | 101.5–102.5 | 100–102 (J. Chem. Soc., 1944, 332) |
| 12b | Tolyl | 60.2 | 115–116 | 116 (Dictionary of Organic Compounds, 1946) |
| 12c | o-Methoxyphenyl | | 85–87 | 89–90 (CRC Handbook of Data on Organic Compounds) |
| 12d | 2-Chlorophenyl | 78.7 | 95.5–96.5 | 96–97 [J. Amer. Chem. Soc. 71, 2644 (1949)] |

-continued

| | | R₁—CH₂—CH₂—COOH [I, R=R₇=R₈=H] | | |
|---|---|---|---|---|
| Example No. | R₁ | Yield, % | M.p. °C. | Literature m.p. °C. |
| 12e | Penyl | 44.5 | 46–47.5 | 48.6 (CRC Handbook) |
| 12f | 2-Thiofuryl | 83.1 | 48–48.5 | 47.5–48 (Bull. Soc. Chim. Fr. 1954, 1349) |

The infrared and $^1$H-NMR spectra of the compounds obtained are in agreement with the structure indicated in the Table.

EXAMPLE 13

Preparation of 3-(3,4,5-trimethoxyphenyl) propionic acid 16.1 g (0.05 mol) of 5-(3,4,5-trimethoxyphenylmethylene)-2,2-dimethyl-1,3-dioxane-4,6-dione (m.p.: 159°–160° C.) were added to 50 ml of the mixture of formic acid and triethylamine prepared as described in Example 1, then the procedure described in Example 2 was followed.

A yield of 10.7 g (89.1%) was achieved, m.p.: 101°–102° C.

The infrared spectrum of the product was identical to that of the substance prepared according to Example 12a.

EXAMPLE 14

Preparation of monoethyl 3-methylglutarate

After weighing in 5.17 g (0.02 mol) of 5-[2-(1-ethoxycarbonyl)propyl]-2,2-dimethyl-1,3-dioxane-4,6-dione (m.p.: 94°–94.5° C.) to 20 ml of the mixture of formic acid and triethylamine prepared as described in Example 1, the reaction mixture was stirred at 100° C. for 2 hours. After cooling down to room temperature 100 ml of ice-water were added, the pH value was adjusted to 1 by adding hydrochloric acid of 1:1 dilution and then extracted 3 times with 150 ml of chloroform each. After combining, the chloroform phase was dried over anhydrous sodium sulfate and filtered, then the chloroform was evaporated under reduced pressure. After adding 20 ml of ether to the oily evaporation residue and standing at 0° C. for 2 hours, the small amount of precipitate was filtered off and the filtrate was evaporated under reduced pressure. The product was obtained as a colourless oily substance.

A yield of 3.20 g (91.8%) was obtained.

IR (KBr): 1700 cm$^{-1}$ (CO)

$^1$H-NMR (CDCl₃, δ ppm): 1.03 (d, 3H, CH₃), 1.23 (t, 3H, CH₃), 2.35 (m, 5H, 2 CH₂ and CH), 4.13 (q, 2H, CH₂).

By the hydrolysis of the above product with sodium hydroxide solution of 20% by weight, 3-methylglutaric acid was obtained, m.p.: 84.5°–86° C. [according to Org. Synth. Coll. Vol. 3, 591 (1955) the literature m.p. is 85°–86° C.].

EXAMPLE 15

Preparation of 5-phenyl-4-pentenoic acid 7.2 g (0.05 mol) of Meldrum's acid and 6.6 g (6.3 ml, 0.05 mol) of cinnamaldehyde were weighed in to 50 ml of the mixture of formic acid and triethylamine prepared as described in Example 1. The reaction mixture was heated to 95° C. during 1 hour and maintained at the same temperature for 2 hours. The product was separated according to Example 1.

A yield of 6.2 g (70.4%) was obtained, m.p.: 83°–86° C.

After recrystallization a small sample of the above product from water, the melting point rose to 88°–90° C. (according to Tetrahedron Lett. 1979, 2325 the literature m.p. is 89°–90° C.).

EXAMPLE 16

Preparation of isocaproic acid

After weighing in 2 g (0.01 mol) of 5-isobutyl-2,2-dimethyl-1,3-dioxane-4,6-dione (m.p.: 120°–122° C.) to 20 ml of the mixture of formic acid and triethylamine prepared as described in Example 1, the reaction mixture was heated at 100° C. for 2 hours, then cooled to room temperature. After adding 40 ml of water and adjusting the pH value to 1 with concentrated hydrochloric acid, the mixture was extracted twice with 50 ml of ether each. After combining the ethereal phase was dried over anhydrous sodium sulfate and the ether was distilled off to give the product as a colourless oil.

A yield of 0.93 g (40%) was achieved.

Based on its IR and $^1$H-NMR spectra, the above product is identical to the commercially available substance.

A small sample of the above product was transformed to isocaproic acid amide, m.p.: 119°–121° C. (according to the CRC Handbook the literature m.p. is 120°–121° C.).

EXAMPLE 17

Preparation of 3-(3,4-dimethoxyphenyl)propionic acid 3.95 g (0.025 mol) of 2-methyl-2-ethyl-1,3-dioxane-4,6-dione and 4.15 g (0.025 mol) of veratraldehyde were weighed in to 25 ml of the mixture of formic acid and triethylamine prepared as described in Example 1. The reaction mixture was heated to 95° C. during 1 hour and maintained at the same temperature for 2 hours, then Example 1 was followed.

A yield of 3.1 g (59.0%) was obtained, m.p.: 95.5°–97.5° C.

EXAMPLE 18

Preparation of 3-(3,4-dimethoxyphenyl)propionic acid

After adding 6.25 ml of the mixture of formic acid and triethylamine prepared as described in Example 1 to 15 ml of dimethylformamide, 3.60 g (0.025 mol) of Meldrum's acid and 4.15 g (0.025 mol) of veratraldehyde were added to the above mixture, which was then heated to 110° C. during 1 hour and reacted at the same temperature for 3 hours. The product was separated from the reaction mixture by the method as described in Example 1.

A yield of 3.9 g (74.2%) was obtained, m.p.: 96°–97° C.

EXAMPLE 19

Preparation of 3-(3,4-dimethoxyphenyl)propionic acid

After weighing in 6.25 ml of the mixture of formic acid and triethylamine (prepared as described in Example 1) to 25 ml of benzene, 4.15 g (0.025 mol) of veratraldehyde and 3.6 g (0.025 mol) of Meldrum's acid were added and the reaction mixture was refluxed for 4 hours. After evaporating the benzene under reduced pressure, 50 ml of water were added to the evaporation residue, the pH value was adjusted to 1 with concentrated hydrochloric acid, then the method of Example 1 was followed.

A yield of 2.5 g (47.6%) was achieved, m.p.: 95°–97° C.

EXAMPLE 20

Preparation of 3-(3,4-dimethoxyphenyl)propionic acid

After adding 2.1 ml of the mixture of formic acid and triethylamine prepared as described in Example 1 to 20 ml of acetonitrile, 3.60 g (0.025 mol) of Meldrum's acid and 4.15 g (0.025 mol) of veratraldehyde were added to the reaction mixture. After heating same to its boiling point (82° C.) within 30 minutes and refluxing it for 4 hours, the acetonitrile was evaporated under reduced pressure, then the method of Example 1 was followed to give 3.6 g of a product, m.p.: 91°–93.5° C., which was recrystallized from aqueous methanol of 50% by volume.

A yield of 2.45 g (46.6%) was achieved, m.p.: 96°–97° C.

EXAMPLE 21

Preparation of 3-(4-nitrophenyl)propionic acid 3.60 g (0.025 mol) of Meldrum's acid and 3.8 g (0.025 mol) of p-nitrobenzaldehyde were weighed in to 25 ml of the mixture of formic acid and triethylamine prepared as described in Example 1. The reaction mixture was heated to 105° C. during 1 hour and reacted at the same temperature for 1 hour. The product was isolated according to Example 1.

A yield of 4.25 g (87.1%) was obtained, m.p.: 159°–162° C.

After recrystallization of a small sample from water, the melting point rose to 162°–164° C. [according to the Dictionary of Organic Compounds (1946) the literature m.p. is 163°–164° C.].

Analysis: Calculated: C 55.4%, H 4.65%, N 7.18%; Found: C552% H 4.80%, N7.05%.

EXAMPLE 22

Preparation of 1,1-di(ethoxycarbonyl)-2-carboxyethane

After weighing in 14.4 g (0.1 mol) of Meldrum's acid and 17.4 g (0.1 mol, 15.5 ml) of diethyl mesoxalate to 100 ml of the mixture of formic acid and triethylamine prepared as described in Example 1, the reaction mixture was heated to 95° C. during 1 hour and reacted at the same temperature for 2 hours. After cooling the reaction mixture to room temperature, adding 350 ml of water and adjusting the pH value to 2 with concentrated hydrochloric acid, the aqueous solution was extracted with 200 ml and then with 100 ml of chloroform. The combined chloroform extract was stirred with 5 g of sodium sulfate and 1 g of activated charcoal at room temperature for 30 minutes, then filtered and the chloroform was distilled off under reduced pressure. After adding 25 ml of diethyl ether to the evaporation residue the mixture was let stand at 0°–5° C. for 16 hours. After filtering the white solid precipitate, ether was evaporated from the filtrate to give the aimed product as a liquid residue.

A yield of 18.55 g (85.0%) was obtained.

IR (KBr): 1730 cm$^{-1}$ (CO)

$^1$H-NMR (CDCl$_3$, δ ppm): 1.29 (t, 6H, 2 CH$_3$), 2.98 (d, 2H, CH$_2$), 3.81 (t, 1H, CH), 4.23 (q, 4H, 2 CH$_2$).

Hydrolysis of a small sample of the above product by 5 molar equivalents of sodium hydroxide in aqueous ethanol gave 1,1,2-tricarboxyethane (ethane-1,1,2-tricarboxylic acid), m.p.: 157°–159° C. (according to Beilstein 2, 812 the literature m.p. is 159° C.).

EXAMPLE 23

Preparation of 3-phenylbutyric acid

After weighing in 2.46 g (0.01 mol) of 5-(1-phenylethylidene)-2,2-dimethyl-1,3-dioxane-4,6-dione (m.p.: 109° C.) to 10 ml of the mixture of formic acid and triethylamine prepared as described in Example 1, the reaction mixture was heated to 105° C. during 30 minutes and reacted at the same temperature for 3 hours. After cooling down to room temperature, 25 ml of water were added to the reaction mixture and its pH value was adjusted to 1 with concentrated hydrochloric acid. The mixture was extracted twice with 25 ml of chloroform each. The combined chloroform phase was extracted twice with 25 ml of 1 N sodium hydroxide solution each and the combined aqueous alkaline phase was again extracted twice with 15 ml of chloroform each. The aqueous phase was stirred with 0.15 g of activated charcoal at room temperature for 30 minutes. After filtering out the charcoal the pH of the filtrate was adjusted to 1 with concentrated hydrochloric acid, then the mixture was extracted 3 times with 15 ml of chloroform each. After drying the combined chloroform solution over anhydrous sodium sulfate and filtering out the drying agent, the filtrate was evaporated under reduced pressure until it became free of chloroform. The evaporation residue was crystallized from petroleum ether.

The title compound was achieved, m.p.: 45.5°–47° C. (according to the CRC Handbook the literature m.p. is 46°–47° C).

EXAMPLE 24

Preparation of isovaleric acid

After weighing in 1.86 g (0.01 mol) of 5-isopropyl-2,2-dimethyl-1,3-dioxane-4,6-dione (m.p.: 103.5°–104° C.) to 5 ml of the mixture of formic acid and triethylamine prepared as described in Example 1, the reaction mixture was heated to 130° C. and reacted at the same temperature for 30 minutes. After cooling the reaction mixture to room temperature the aimed product was separated as described in Example 23.

The title compound was obtained.

The above product was transformed to isovaleric acid amide, m.p.: 136° C. (according to the CRC Handbook the literature m.p. is 135°–137° C.).

EXAMPLE 25

Preparation of monoethyl 3,4-dimethoxybenzylmalonate monohydrate

A reaction mixture containing 16.6 g (0.1 mol) of veratraldehyde, 14.4 g (0.1 mol) of Meldrum's acid, 80 ml of ethanol and 25 ml of the mixture of formic acid and triethylamine prepared as described in Example 1 was heated to the boiling point during 1 hour and then refluxed for 4 hours. After evaporating the ethanol under reduced pressure, 100 ml of ice-water were added to the evaporation residue. The pH value was adjusted to 1 with concentrated hydrochloric acid and the mixture was extracted twice with 100 ml of chloroform each. The combined chloroform extract was extracted twice with 120 ml of saturated aqueous sodium hydrogen carbonate solution each, the combined aqueous extract was stirred with 2 g of activated charcoal at 10° C. for 30 minutes, then the charcoal was filtered off. After adding ice to the filtrate and adjusting its pH value to 1 with concentrated hydrochloric acid, the reaction mixture was allowed to stand at 5° C. for 16 hours. Subsequently, the crystalline precipitate was filtered, washed with water 3 times and dried to constant weight. When dried under reduced pressure at room temperature, the product obtained loses one molar equivalent of water and liquefies to a honey-like substance again becoming crystalline after adding water.

A yield of 14.35 g (47.8%) was achieved, m.p.: 51°–54° C.

After recrystallizing a small sample of this product from a mixture of methanol and water, the melting point rose to 56°–57° C.

IR (KBr): 1725 cm$^{-1}$ (CO)

$^1$H-NMR (CDCl$_3$, δ ppm): 1.23 (t, 3H, CH$_3$), 3.20 (d, 2H, CH$_2$), 3.68 (t, 1H, CH) , 3.85 (s, 6H, 2OCH$_3$) , 4.18 (q, 2H, CH$_2$), 6.76 (m, 3H, aromatic).

EXAMPLE 26

Preparation of monomethyl 3,4-dimethoxybenzylmalonate

A reaction mixture containing 16.6 g (0.1 mol) of veratraldehyde, 14.4 g (0.1 mol) of Meldrum's acid, 80 ml of methanol and 25 ml of the mixture of formic acid and triethylamine prepared as described in Example 1 was heated to its boiling point during 1 hour and then refluxed for 6 hours. After evaporating methanol under reduced pressure, 100 ml of ice-water were added to the evaporation residue, the pH value was adjusted to 1 with concentrated hydrochloric acid and the mixture was extracted twice with 100 ml of chloroform each. The combined chloroform extract was extracted twice with 120 ml of saturated aqueous sodium hydrogen carbonate solution each. The combined aqueous extract was stirred with activated charcoal at 10° C. for 30 minutes, then the charcoal was filtered out and after adding ice to the filtrate, its pH value was adjusted to 1 with concentrated hydrochloric acid. The mixture was extracted twice with 60 ml of chloroform each and the combined chloroform solution was washed with 120 ml of water. After drying the chloroform solution over anhydrous sodium sulfate and filtering, the filtrate was evaporated under reduced pressure until it became chloroform-free. The evaporation residue was dissolved in 50 ml of diethyl ether and stirred with 1 g of activated charcoal for 30 minutes. After filtering the charcoal, petroleum ether was dropwise added to the filtrate at 5° C. The first separated oily material of small amount was separated in a shaking funnel and the upper solvent phase was evaporated under reduced pressure until solvent-free. The aimed product was obtained as a honey-like substance.

A yield of 12.7 g (47.3%) was achieved.

IR (KBr): 1730 cm$^{-1}$ (CO)

$^1$H-NMR (CDCl$_3$, δ ppm): 3.18 (d, 2H, CH$_2$), 3.50 (t, 1H, CH), 3.70 (s, 3H, COOCH$_3$) , 3.84 (s, 6H, 2 OCH$_3$) , 6.75 (m, 3H, aromatic).

EXAMPLE 27

Preparation of mono-n-butyl 3,4-dimethoxybenzylmalonate

A reaction mixture containing 16.6 g (0.1 mol) of veratraldehyde, 14.4 g (0.1 mol) of Meldrum's acid, 80 ml of n-butanol and 25 ml of the mixture of formic acid and triethylamine prepared as described in Example 1 was heated to 95° C. during 1 hour and reacted at the same temperature for 2 hours. Subsequently, Example 26 was followed to give the aimed product in a honey-like form.

A yield of 11.9 g (38.3%) was obtained.

IR (KBr): 1730 cm$^{-1}$ (CO)

$^1$H-NMR (CDCl$_3$, δ ppm): 0.89 (t, 3H, CH$_3$), 1.30 (m, 2H, CH$_2$), 1.56 (m, 2H, CH$_2$), 3.20 (d, 2H, φ-CH$_2$), 3.69 (t, 1H, CH) , 3.88 (s, 6H, 2OCH$_3$) , 4.13 (t, 2H, COOCH$_2$) , 6.76 (m, 3H, aromatic).

EXAMPLE 28

Preparation of monoethyl 3,4,5-trimethoxybenzylmalonate 80 ml of ethanol, 19.6 g (0.1 mol) of 3,4,5-trimethoxybenzaldehyde and 14.4 g (0.1 mol) of Meldrum's acid were weighed in to 25 ml of the mixture of formic acid and triethylamine prepared as described in Example 1, then the procedure of Example 25 was followed.

A yield of 15.3 g (49.0%) was obtained, m.p.: 75°–80° C.

After recrystallizing a small sample of this product from a mixture of acetone and water, the melting point rose to 83°–85° C.

IR (KBr): 1725 cm$^{-1}$ (CO)

$^1$H-NMR (CDCl$_3$, δ ppm): 1.23 (t, 3H, CH$_3$), 3.19 (d, 2H, CH$_2$), 3.70 (t, 1H, CH), 3.81 (s, 9H, 3OCH$_3$), 4.20 (q, 2H, COOCH$_2$), 6.43 (s, 2H, aromatic).

EXAMPLE 29

Preparation of monoethyl 3,4-dimethoxybenzylmalonate monohydrate 2.94 g (0.01 mol) of 5-(3,4-dimethoxyphenylmethyl)-2,2-dimethyl-1,3-dioxane-4,6-dione (m.p.: 142°–144° C.) and 0.83 ml of the mixture containing formic acid and triethylamine prepared as described in Example 1 were added to 8 ml of ethanol. After refluxing the reaction mixture for 6 hours, the method described in Example 25 was followed. The crude product was crystallized from a mixture of methanol and water.

A yield of 2.05 g (63.3%) was obtained, m.p.: 56°–57° C.

Other quality characteristics of the above product were in agreement with those of the product prepared according to Example 25.

EXAMPLE 30

Preparation of ethyl 3-(3,4-dimethoxyphenyl)propionate

After weighing in 20 ml of ethanol, 4.15 g (0.025 mol) of veratraldehyde and 3.6 g (0.025 mol) of Meldrum's acid to 6.25 ml of the mixture of formic acid and triethylamine prepared as described in Example 1, the reaction mixture was heated to its boiling point during 1 hour and refluxed for 4 hours. Ethanol was distilled off under environmental pressure, then the temperature of the reaction mixture was raised to 120° C. and the mixture was reacted at the same temperature for 3 hours. After cooling the reaction mixture to room temperature, the residue was dissolved in 100 ml of chloroform and successively extracted with 50 ml of 1 N hydrochloric acid, twice with 50 ml of saturated sodium hydrogen carbonate solution each and finally with 50 ml of water. After drying the chloroform phase over anhydrous sodium sulfate and filtering, the filtrate was evaporated under reduced pressure until chloroform-free. The evaporation residue was dissolved in diethyl ether and petroleum ether was added dropwise to this solution until it became constantly opalescent. The mixture was let stand at −10° C. for 3 days, then the crystalline precipitate was filtered and washed with petroleum ether cooled to −10° C.

A yield of 4.25 g (71.3%) was obtained, m.p.: 11°–13° C. (according to Beilstein 10, II, 279 the literature m.p. is 13° C.).

The infrared and $^1$H-NMR spectra of the above product were found to be in complete agreement with those of ethyl 3-(3,4-dimethoxyphenyl) propionate prepared by the esterification of 3-(3,4-dimethoxyphenyl)propionic acid.

Preparation of methyl 3-(3,4-dimethoxyphenyl)propionate

After adding 80 ml of methanol, 16.6 g (0.1 mol) of veratraldehyde and 14.4 g (0.1 mol) of Meldrum's acid to 6.25 ml of the mixture of formic acid and triethylamine prepared as described in Example 1, the reaction mixture was heated to its boiling point during 1 hour and refluxed for 6 hours. After distilling off the methanol under environmental pressure the reaction mixture was heated at 115° C. for 2 hours, then cooled down to room temperature and dissolved in 200 ml of chloroform. The chloroform solution was successively extracted with 200 ml of 1 N hydrochloric acid, 120 ml of saturated aqueous sodium hydrogen carbonate solution and 100 ml of water. After adding 5 g of sodium sulfate and 1 g of activated charcoal, the chloroform solution was stirred for 30 minutes, then filtered and evaporated under reduced pressure until it became chloroform-free. The evaporation residue was diluted with 50 ml of petroleum ether and let stand at −15° C. for 48 hours. After filtering out a small amount of solid precipitate, the two-phase liquid was evaporated under reduced pressure until solvent-free and then fractionally distilled under reduced pressure. The aimed product boiled at 125°–130° C./400 Pa.

A yield of 13.9 g (62.0%) was obtained.

IR (KBr): 1735 cm$^{-1}$ (CO)

$^1$H-NMR (CDCl$_3$, δ ppm): 2.60 (t, 2H, CH$_2$), 2.90 (t, 2H, CH$_2$), 3.66 (s, 3H, COOCH$_3$), 4.86 (s, 6H, 2OCH$_3$), 6.76 (m, 3H, aromatic).

EXAMPLE 32

Preparation of n-butyl 3-(3,4-dimethoxyphenyl)propionate

A reaction mixture Containing 16.6 g (0.1 mol) of veratraldehyde, 14.4 g (0.1 mol) of Meldrum's acid, 80 ml of n-butanol and 6.25 ml of the mixture of formic acid and triethylamine prepared as described in Example 1 was heated to 100° C. during 1 hour and reacted at the same temperature for 2 hours, then at 110° C. for 3 hours. After distilling off the butanol under reduced pressure, the reaction mixture was cooled to room temperature and dissolved in 200 ml of chloroform, then the procedure of Example 31 was followed. The crude product obtained was purified by fractional distillation. The aimed compound boiled at 111°–113° C./400 Pa.

A yield of 20.1 g (75.5%) was achieved.

IR (KBr): 1735 cm$^{-1}$ (CO)

$^1$H-NMR (CDCl$_3$, δ ppm): 0.92 (t, 3H, CH$_3$), 1.34 (m, 2H, CH$_2$), 1.58 (m, 2H, CH$_2$), 2.60 (t, 2H, CH$_2$), 2.90 (t, 2H, CH$_2$), 3.82 (s, 6H, 2OCH$_3$), 4.07 (t, 2H, COOCH$_2$), 6.75 (m, 3H, aromatic).

EXAMPLE 33

Preparation of ethyl 3-(3,4,5-trimethoxyphenyl)propionate

A reaction mixture containing 4.9 g (0.025 mol) of 3,4,5-trimethoxybenzaldehyde, 3.6 g (0.025 mol) of Meldrum's acid, 20 ml of ethanol and 6.25 ml of the mixture of formic acid and triethylamine prepared as described in Example 1 was boiled to its boiling point during 1 hour and refluxed for 4 hours. After distilling off the ethanol under environmental pressure, the residue was reacted at 130° C. for 2 hours, then the procedure of Example 31 was followed. The crude product was purified by fractional distillation under reduced pressure. The aimed product boiled at 132°–134° C./400 Pa.

A yield of 5.6 g (83.5%) was obtained.

IR (KBr): 1735 cm$^{-1}$ (CO)

$^1$H-NMR (CDCl$_3$, δ ppm): 1.25 (t, 3H, CH$_3$), 2.61 (t, 2H, CH$_2$), 2.90 (t, 2H, CH$_2$), 3.80 (s, 3H, OCH$_3$), 3.83 (s, 6H, 2 OCH$_3$), 4.14 (q, 2H, COOCH$_2$), 6.41 (s, 2H, aromatic).

EXAMPLE 34

Preparation of 3-(3,4-dimethoxyphenyl)propionic acid

A reaction mixture containing 14.4 g (0.1 mol) of Meldrum's acid, 16.6 g (0.1 mol) of veratraldehyde, 100 ml of ethyl acetate and 25 ml of the mixture of formic acid and triethylamine prepared as described in Example 1 was heated to its boiling point during 1 hour and then refluxed for 6 hours. After distilling off the ethyl acetate under reduced pressure, the distillation residue was cooled to room temperature, 100 ml of water were added and the pH value of the mixture was adjusted to 1 with concentrated hydrochloric acid, then the method described in Example 1 was followed.

A yield of 11.65 g (55.4%) was obtained, m.p.: 94°–96° C.

Other quality characteristics of the product were identical to those given in Example 1.

EXAMPLE 35

Preparation of 3-(3,4-dimethoxyphenyl)propionic acid

After dropwise adding 27.2 g (33.1 ml, 0.24 mol) of 1-ethylpiperidine to 27.6 g (22.6 ml, 0.6 mol) of formic acid under stirring, 7.2 g (0.05 mol) of Meldrum's acid and 8.3 g (0.05 mol) of veratraldehyde were added to the solution which was then heated to 95° C. during 1 hour and reacted at the same temperature for 2 hours. Subsequently the method of Example 1 was followed.

A yield of 7.4 g (70.4%) was obtained, m.p.: 96.5°–97.5° C.

Based on its infrared spectrum, this product was found to be identical to that described in Example 1.

EXAMPLE 36

Preparation of 3-(3,4-dimethoxyphenyl) propionic acid

After dropwise adding 17.55 g (25 ml, 0.24 mol) of diethylamine to 27.6 g (22.6 ml, 0.6 mol) of formic acid under stirring and cooling, 7.2 g (0.05 mol) of Meldrum's acid and 8.3 g (0.05 mol) of veratraldehyde were added to the above mixture, then the procedure of Example 35 was followed.

A yield of 5.75 g (54.7%) was achieved, m.p.: 95°–96° C.

The infrared spectrum of this product was found to be identical to that of the substance obtained in Example 1.

EXAMPLE 37

Preparation of 3-(3,4-dimethoxyphenyl)propionic acid

After dropping 20.4 g (23.7 ml, 0.24 mol) of piperidine to 27.6 g (22.6 ml, 0.6 mol) of formic acid under stirring and cooling, 7.2 g (0.05 mol) of Meldrum's acid and 8.3 g (0.05 mol) of veratraldehyde were added to the above mixture, then the procedure of Example 35 was followed.

A yield of 5.83 g (55.5%) was obtained, m.p.: 96°–97.5° C.

Based on the infrared spectrum, this product was found to be identical to that prepared in Example 1.

EXAMPLE 38

Preparation of 3-(3,4-dimethoxyphenyl) propionic acid

After dropping 20.9 g (20.9 ml, 0.24 mol) of morpholine to 27.6 g (22.6 ml, 0.6 mol) of formic acid under stirring and cooling, 7.2 g (0.05 mol) of Meldrum's acid and 8.3 g (0.05 mol) of veratraldehyde were added to the mixture and subsequently the procedure of Example 35 was followed.

The title compound was obtained, m.p.: 94°–96° C.

Based on the infrared spectrum, this product was found to be identical to that prepared in Example 1.

EXAMPLE 39

Preparation of 3-(4-methylthiophenyl)propionic acid

After weighing in 7.2 g (0.05 mol) of Meldrum's acid and 7.6 g (6.5 ml, 0.05 mol) of 4-methylthiobenzaldehyde to 50 ml of the mixture of formic acid and triethylamine prepared as described in Example 1, the temperature of the reaction mixture was increased to 95° C. during 1 hour and reacted at the same temperature for 2 hours, then cooled down to room temperature. After adding 75 ml of water and adjusting the pH value to 1 with concentrated hydrochloric acid, the mixture was extracted twice with 50 ml of chloroform each. The combined chloroform solution was extracted twice with 100 ml of 1 N sodium hydroxide solution each. The combined aqueous alkaline phase was stirred with 0.5 g of activated charcoal at room temperature for 30 minutes, then the charcoal was filtered off. After adding 20 g of ice to the filtrate and adjusting its pH value to 1 with concentrated hydrochloric acid, the mixture was let stand at 5° C. for 24 hours. The crystalline precipitate was filtered and washed with water cooled to 0° C.

A yield of 6.5 g (66.3%) was achieved, m.p.: 98°–100° C.

After recrystallizing a small sample of the above product from a mixture of acetone and water, the melting point raised to 100°–100.5° C.

IR (KBr): 1710 cm$^{-1}$ (CO)

$^1$H-NMR (CDCl$_3$, δ ppm): 2.48 (s, 3H, SCH$_3$), 2.68 (t, 2H, CH$_2$), 2.94 (t, 2H, CH$_2$), 7.18 (m, 4H, aromatic).

EXAMPLE 40

Preparation of 3-(4-dimethylaminophenyl)propionic acid

After adding 13.8 g (0.05 mol) of 5-(4-dimethylaminophenylmethylene)-2,2-dimethyl-1,3-dioxane-4,6-dione to 100 ml of the mixture of formic acid and triethylamine prepared as described in Example 1, the temperature of the reaction mixture was increased to 95° C. during 1 hour while stirring and reacted at the same temperature for 2 hours. After cooling to room temperature, 200 ml of water were added and the mixture was extracted twice with 150 ml of chloroform each. The combined chloroform extract was washed with 50 ml of saturated saline solution. The chloroform solution was evaporated until it became chloroform-free. The evaporation residue, which became solid on cooling down, was dissolved at room temperature in 70 ml of acetone and, after filtering out a small amount of insoluble material, the filtrate was stirred with 0.5 g of activated charcoal for 30 minutes, then the charcoal was filtered. After evaporating the acetone filtrate under reduced pressure to about one fourth of its volume, it was set aside at 5° C. for 2 days for crystallization. The crystalline precipitate was filtered and washed with acetone cooled to 0° C. After combining with the washings, the mother liquor was concentrated by evaporation under reduced pressure, then ethyl acetate was added to the residue, it was let stand at 5° C. and then filtered.

A yield of 5.85 g (60.5%) was achieved, m.p.: 94°–97° C.

A small sample of the product was recrystallized twice from a mixture of ethanol and water to give a crystalline product, m.p.: 107°–108° C.

IR (KBr): 1710 cm$^{-1}$ (CO)

$^1$H-NMR (CDCl$_3$, δ ppm): 2.66 (t, 2H, CH$_2$), 2.86 (t, 2H, CH$_2$), 2.93 (s, 6H, 2 CH$_3$), 6.73 (d, 2H, aromatic), 7.10 (d, 2H, aromatic).

We claim:

1. A process for the preparation of carboxylic acids, and their derivatives, of the formula $$\begin{array}{c} R \\ \diagdown \\ \diagup \\ R_1 \end{array} C - \underset{\underset{H}{|}}{\overset{\overset{R_8}{|}}{C}} - \overset{O}{\overset{\|}{C}} - O - R_7, \qquad I$$

wherein

R means hydrogen, or a C$_{1-4}$alkyl or a (C$_{1-5}$alkoxy)carbonyl group,

R$_1$ stands for a C$_{1-6}$alkyl group, a (C$_{1-5}$alkoxy)-carbonyl group, a (C$_{1-5}$alkyl)carbonyl group, a (C$_{1-5}$alkoxy)carbonyl(C$_{1-5}$alkyl) group, a phenyl group, optionally monosubstituted by a C$_{1-4}$alkyl or C$_{2-4}$alkenyl group, di- or tri- substituted by C$_{1-4}$alkoxy groups, monosubstituted by a nitro group, disubstituted by C$_{1-4}$alkoxy and hydroxy groups, monosubstituted by a C$_{1-4}$alkylthio group, mono-or disubstituted by one or two di(C$_{1-4}$alkyl) amino groups or monosubstituted by halogen, for a furyl group, for a thiofuryl group, for a thienyl group, or for a group of the formula

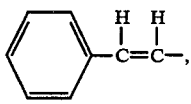

or R and R₁ together form a straight-chain $C_{4-5}$alkylene group,

R₇ stands for hydrogen or a $C_{1-7}$alkyl group and

R₈ means hydrogen or a carboxyl group, which process comprises reacting a 1,3-dioxane-4,6-dione derivative of the formula

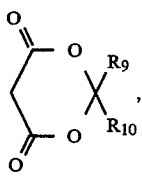   III wherein

R₉ stands for a $C_{1-4}$alkyl group or a phenyl group, optionally monosubstituted by halogen, and R₁₀ stands for hydrogen or a $C_{1-5}$alkyl group, or R₉ and R₁₀ together form a pentamethylene group, and an aldehyde or ketone of the formula

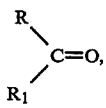   II wherein

R and R₁ are as defined above, in the presence of formic acid and of 1 or more members selected from the group consisting of secondary amines and tertiary amines and, optionally of an alcohol of the formula $$R_7-OH \qquad VI,$$

wherein

R₇ is a $C_{1-7}$alkyl group, at a temperature of 20° to 140° C. optionally in the presence of an inert organic solvent.

2. The process of claim 1, wherein the inert organic solvent is at least one member selected from the group consisting of benzene, dimethylformamide, acetonitrile, and ethyl acetate.

3. The process of claim 1, wherein the amine is at least one member selected from the group consisting of di-($C_{1-4}$alkyl)amine, tri-($C_{1-4}$alkyl)amine and cyclic amine.

4. The process of claim 1, wherein the amine is at least one member selected from the group consisting of dimethylamine, diethylamine, methylethylamine, triethylamine, pyridine, piperidine, N-($C_{1-4}$alkyl)-piperidine, and morpholine.

5. The process of claim 4, wherein the amine is n-ethylpiperidine.

6. The process of claim 1, wherein 1 to 20 moles of formic acid are present for each mole of the compound of formula III.

7. The process of claim 6, wherein 3 to 6 moles of formic acid are present for each mole of the compound of formula III.

8. The process of claim 6, wherein 0.1 to 1.0 mole of the amine is present for each mole of formic acid.

9. The process of claim 8, wherein 0.1 to 0.5 mole of the amine is present for each mole of formic acid.

* * * * *

UNITED STATES PATENT AND TRADEMARK OFFICE
CERTIFICATE OF CORRECTION

PATENT NO.   : 5,350,872
DATED        : September 27, 1994
INVENTOR(S)  : Toth et al.

It is certified that error appears in the above-indentified patent and that said Letters Patent is hereby corrected as shown below:

Column 22, claim 1, line 59
  "$C_{1-5}$alkyl" should read -- $C_{1-4}$alkyl --

Signed and Sealed this

Thirteenth Day of December, 1994

*Attest:*

BRUCE LEHMAN

*Attesting Officer*    *Commissioner of Patents and Trademarks*